US012744945B2

(12) United States Patent
Sun

(10) Patent No.: US 12,744,945 B2
(45) Date of Patent: Sep. 22, 2026

(54) METHOD AND APPARATUS FOR DETERMINING CLICK-FARMING IN LIVE ROOM

(71) Applicant: SHANGHAI BILIBILI TECHNOLOGY CO., LTD., Shanghai (CN)

(72) Inventor: Yuanyuan Sun, Shanghai (CN)

(73) Assignee: SHANGHAI BILIBILI TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/715,725

(22) PCT Filed: Jun. 17, 2022

(86) PCT No.: PCT/CN2022/099476
§ 371 (c)(1),
(2) Date: Jun. 2, 2024

(87) PCT Pub. No.: WO2023/098030
PCT Pub. Date: Jun. 8, 2023

(65) Prior Publication Data
US 2025/0039472 A1 Jan. 30, 2025

(30) Foreign Application Priority Data
Dec. 1, 2021 (CN) ......................... 202111454994.0

(51) Int. Cl.
*H04N 21/2187* (2011.01)
*A61B 5/024* (2006.01)
(Continued)

(52) U.S. Cl.
CPC ......... *H04N 21/2187* (2013.01); *A61B 5/024* (2013.01); *H04N 21/44204* (2013.01); *H04N 21/4788* (2013.01)

(58) Field of Classification Search
CPC ......... H04N 21/2187; H04N 21/44204; H04N 21/4788
See application file for complete search history.

(56) References Cited

U.S. PATENT DOCUMENTS 8,561,184 B1 * 10/2013 Marsa .................. H04L 67/535 726/22
10,129,288 B1 11/2018 Xie et al.
(Continued)

FOREIGN PATENT DOCUMENTS

CN 104217087 A 12/2014
CN 107169768 A 9/2017
(Continued)

OTHER PUBLICATIONS

International Patent Application No. PCT/CN2022/099476; Int'l Search Report; dated Sep. 19, 2022; 2 pages.
(Continued)

*Primary Examiner* — Joshua D Taylor
(74) *Attorney, Agent, or Firm* — BakerHostetler

(57) ABSTRACT

This application provides a method and an apparatus for determining click-farming in a live room. The method for determining click-farming in a live room includes: determining user distribution information associated with a target live room, and determining a user distribution ratio based on the user distribution information; obtaining population density distribution information, and determining a population density distribution ratio based on the population density distribution information; and determining whether click-farming exists in the target live room based on the user distribution ratio and the population density distribution ratio. This method enriches means for determining click-farming in the live room, and effectively improves accuracy of determining click-farming.

19 Claims, 5 Drawing Sheets

(51) Int. Cl.

| | |
|---|---|
| ***H04N 21/442*** | (2011.01) |
| ***H04N 21/4788*** | (2011.01) |

(56) References Cited

U.S. PATENT DOCUMENTS

| | | | | |
|---|---|---|---|---|
| 12,361,447 | B2 * | 7/2025 | Libell | G06Q 30/0248 |
| 2016/0267490 | A1 | 9/2016 | Johnson | |
| 2022/0159022 | A1 * | 5/2022 | Aghamirzaei | G06Q 30/0248 |
| 2023/0156024 | A1 * | 5/2023 | Olson | G06Q 30/0248<br>726/23 |
| 2023/0367833 | A1 * | 11/2023 | Kol | G06F 16/958 |
| 2024/0146691 | A1 * | 5/2024 | Sun | H04L 63/1425 |
| 2025/0039472 | A1 * | 1/2025 | Sun | H04N 21/44204 |

FOREIGN PATENT DOCUMENTS

| | | | |
|---|---|---|---|
| CN | 107454441 | A | 12/2017 |
| CN | 109413439 | A | 3/2019 |
| CN | 110855717 | A | 2/2020 |
| CN | 112633766 | A | 4/2021 |
| CN | 113067808 | A | 7/2021 |
| CN | 113938318 | A | 1/2022 |

OTHER PUBLICATIONS

Yanjing et al.; “Research of the data user’s mobile phone number in anti-cheating”; Intelligent Computer and Application; vol. 9 No. 3; May 2019; p. 256, 257, 258 and 262 (contains English Abstract).

* cited by examiner current
Shanghai 254
Sichuan 137
Liaoning 95
Tianjin 62
Shandong 51
Province/City 42
Hunan 33

METHOD AND APPARATUS FOR DETERMINING CLICK-FARMING IN LIVE ROOM

CROSS-REFERENCE TO RELATED APPLICATIONS

This application is the U.S. National Stage of International Application No. PCT/CN2022/099476, filed on Jun. 17, 2022, which claims priority to Chinese Patent Application No. 202111454994.0, filed on Dec. 1, 2021, and entitled "METHOD AND APPARATUS FOR DETERMINING CLICK-FARMING IN LIVE ROOM", which are incorporated herein by reference in their entireties.

TECHNICAL FIELD

This application relates to the field of network livestreaming technologies, and in particular, to a method for determining click-farming in a live room. This application also relates to an apparatus for determining click-farming in a live room, a computing device, a computer-readable storage medium, and a computer program.

BACKGROUND

With improvement of a network communication technology and acceleration of a broadband network, livestreaming has seen greater development and application. In an existing livestreaming system, popularity is an important indicator for ranking rooms of a livestreaming platform. Usually, higher popularity indicates a higher ranking and a higher possibility that an online streamer is watched by a user. A real-time quantity of viewers in a live room is a key part in popularity calculation. Consequently, to improve popularity, some online streamers use illegal means to simulate viewing of live rooms, and forge quantities of online viewers in the live rooms, that is, improve popularity rankings through click-farming. Therefore, how to accurately determine whether click-farming exists in a live room is an important means to maintain ecological stability of a livestreaming platform.

Currently, it is determined whether click-farming exists in the live room by determining whether there is a steep increase or a jitter in a total person quantity of the live room. This determining method is single, and an error in determining sometimes occurs.

SUMMARY

In view of this, an embodiment of this application provides a method for determining click-farming in a live room. This application also relates to an apparatus for determining click-farming in a live room, a computing device, a computer-readable storage medium, and a computer program, to resolve a problem in the conventional technology that a method for determining whether click-farming exists in a live room is single, and accuracy is relatively low.

According to a first aspect of the embodiments of this application, a method for determining click-farming in a live room is provided and includes:

collecting user distribution information of a target live room, and determining a user distribution ratio based on the user distribution information;

obtaining population density distribution information, and determining a population density distribution ratio based on the population density distribution information; and determining, according to the user distribution ratio and the population density distribution ratio, whether click-farming exists in the target live room.

According to a second aspect of the embodiments of this application, an apparatus for determining click-farming in a live room is provided and includes:

a collection means, configured to collect user distribution information of a target live room, and determine a user distribution ratio based on the user distribution information;

an obtaining means, configured to obtain population density distribution information, and determine a population density distribution ratio based on the population density distribution information; and a determining means, configured to determine, according to the user distribution ratio and the population density distribution ratio, whether click-farming exists in the target live room.

According to a third aspect of the embodiments of this application, a computing device is provided and includes a memory, a processor, and computer instructions stored in the memory and capable of being run on the processor. The processor executes the computer instructions to implement the steps of the method for determining click-farming in a live room.

According to a fourth aspect of the embodiments of this application, a computer-readable storage medium is provided and stores computer instructions. The computer instructions are executed by a processor to implement the steps of the method for determining click-farming in a live room.

According to a fifth aspect of the embodiments of this application, a computer program is provided. When the computer program is executed on a computer, the computer is enabled to perform steps of the method for determining click-farming in a live room.

The method for determining click-farming in a live room provided in this application includes: collecting user distribution information of a target live room, and determining a user distribution ratio based on the user distribution information; obtaining population density distribution information, and determining a population density distribution ratio based on the population density distribution information; and determining, according to the user distribution ratio and the population density distribution ratio, whether click-farming exists in the target live room.

According to the embodiments of this application, the user distribution density of the live room is monitored, and whether click-farming exists in the live room is determined with reference to actual population density. This enriches means for determining click-farming in the live room, and effectively improves accuracy of determining click-farming.

DESCRIPTION OF EMBODIMENTS

Figures 1, 2:
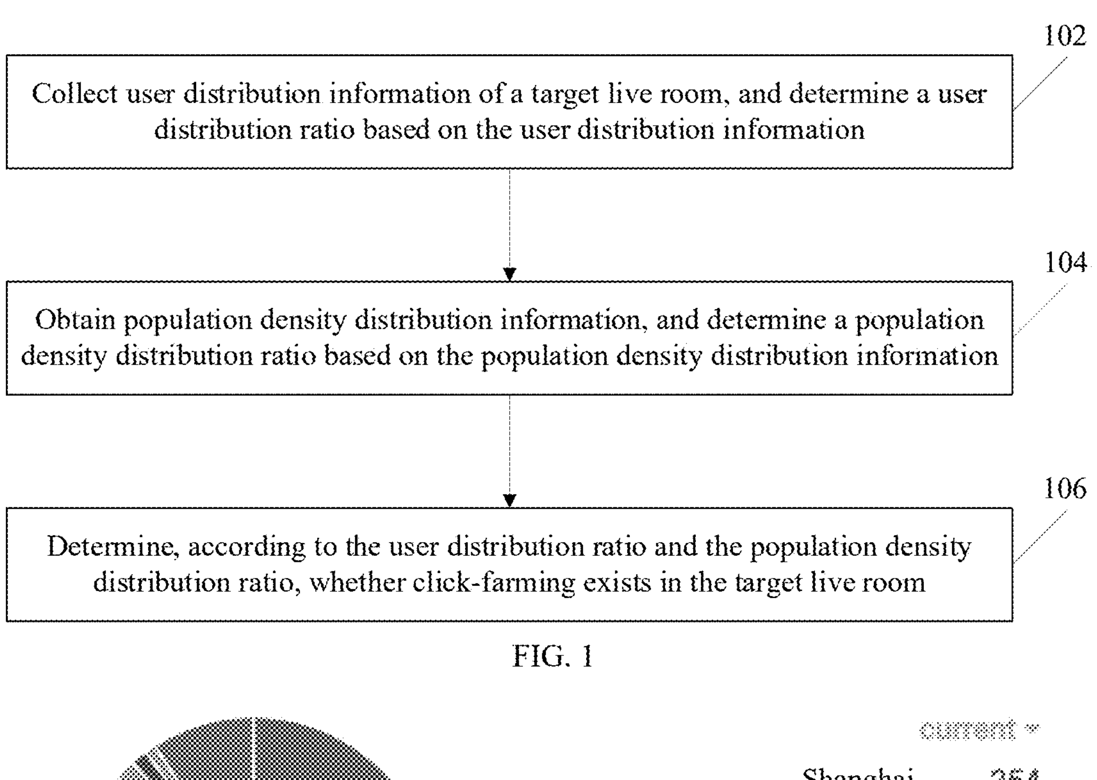
FIG. 1 is a flowchart of a method for determining click-farming in a live room according to an embodiment of this application.
FIG. 2 is a schematic diagram of a user distribution ratio of a live room according to an embodiment of this application.

Many specific details are described in the following descriptions to facilitate full understanding of this application. However, this application can be implemented in many other manners different from those described herein. A person skilled in the art can make similar promotion without departing from the connotation of this application. Therefore, this application is not limited to specific implementations disclosed below.

Terms used in one or more embodiments of this application are merely used to describe specific embodiments, and are not intended to limit the one or more embodiments of this application. The terms "a", "the", and "said" of singular forms used in one or more embodiments and the appended claims of this application are also intended to include plural forms, unless otherwise specified in the context clearly. It should be further understood that the term "and/or" used in one or more embodiments of this application indicates and includes any or all possible combinations of one or more associated listed items.

It should be understood that although the terms such as "first" and "second" may be used in one or more embodiments of this application to describe various types of information, the information should not be limited to these terms. These terms are merely used to distinguish between information of a same type. For example, without departing from the scope of the one or more embodiments of this application, "first" may also be referred to as "second", and similarly, "second" may also be referred to as "first". Depending on the context, for example, the word "if" used herein can be interpreted as "while", "when", or "in response to determining". Terms used in one or more embodiments of this application are explained first.

Live popularity: refers to a value calculated based on a specific ratio by integrating a quantity of viewers, a quantity of bullet-screen comments, a quantity of gifts, and the like. The live popularity is used for ranking based on popularity at a livestreaming platform.

Click-farming: refers to a case in which a large amount of false viewing is generated by simulating normal user access, that is, simulating viewing of a live room by using an illegal means. In a livestreaming system, popularity is an important indicator for ranking rooms of a livestreaming platform. Usually, higher popularity indicates a higher ranking and a higher possibility that an online streamer is watched by a user. It is of great significance for maintaining ecology of the livestreaming platform by precisely determining whether click-farming exists in a live room, and taking a specific punishment measure for a room in which click-farming exists. In a formula for calculating the popularity, most basic data is an online person quantity. A calculation mode of the online person quantity is periodic heartbeat reporting, that is, a manner in which a client computing device associated with each viewing user passes a scheduled task. A heartbeat is reported by the client computing device as long as a user is on a playing page of the livestreaming platform, and a server computing device monitors a quantity of online users by counting a quantity of heartbeats reported by client computing devices associated with users of the livestreaming platform. If an algorithm of a click-farmer for simulating heartbeat reporting is perfect, an effect same as real viewing is produced, and a purpose of click-farming in the live room is achieved.

Based on this, this application provides a method for determining click-farming in a live room. This application also relates to an apparatus for determining click-farming in a live room, a computing device, a computer-readable storage medium, and a computer program. The method for determining click-farming in a live room, the apparatus for determining click-farming in a live room, the computing device, the computer-readable storage medium, and the computer program are described in detail in the following embodiments one by one.

FIG. 1 is a flowchart of a method for determining click-farming in a live room according to an embodiment of this application. The method specifically includes the following steps:

Step 102: Collect user distribution information of a target live room, and determine a user distribution ratio based on the user distribution information.

The user distribution information specifically is address distribution information of users viewing livestreaming in a live room. In actual application, obtaining of a quantity of actual viewers in a room depends on heartbeat reporting of terminal devices (i.e., client computing devices) used by users. After each user enters the live room, the terminal device used by each user periodically reports viewing behavior of the user to a server computing device. Reported content mainly includes content such as a room number (room identifier), a terminal IP address, a terminal type, and terminal system information. After receiving reporting, the server positions the user according to the terminal IP address, positions location information of the user, and collects statistics on the location information, to obtain user distribution information of an actual viewing user of the target live room.

The target live room is a live room that needs to be determined whether click-farming exists. For example, if currently it is necessary to determine whether click-farming exists in a live room 1, the live room 1 is a target live room. If it is necessary to be determined whether click-farming exists in a live room 2, the live room 2 is a target live room. Before the user distribution information of the target live room is collected, the target live room needs to be first determined.

In actual application, a person quantity of each live room varies. If a person quantity of a live room is relatively small, and click-farming obviously does not exist, the live room does not need to be determined. Therefore, determining the target live room includes:

- determining an initial live room on a livestreaming platform, and obtaining a live room person quantity of the initial live room; and
- when the live room person quantity exceeds a preset person quantity threshold, determining the initial live room as a target live room.

Specifically, the livestreaming platform is a platform providing various livestreaming for a user. An online streamer creates a live room on the livestreaming platform for livestreaming. The user may enter a live room by using the livestreaming platform for viewing livestreaming. The initial live room is determined on the livestreaming platform, for determining whether livestreaming click-farming needs to be determined for the initial live room. After the initial live room is determined, the live room person quantity of the initial live room is obtained. When the live room person quantity exceeds the preset person quantity threshold, the initial live room is determined as the target live room. For example, for a live room, a quantity of viewers is only 10, and in this case, it is not necessary to determine whether click-farming exists in the live room. Because there is too little data, there is no global same attribute. The initial live room is determined only after the live room person quantity of the initial live room exceeds a specific quantity. By screening the live room person quantity, a live room with an insufficient person quantity can be filtered out, and there is no need to determine the live room with the insufficient person quantity, reducing calculation pressure of the server and effectively improving resource utilization.

In a specific implementation provided in this application, the initial live room is determined as the live room 1 on the livestreaming platform. A live room person quantity of the live room 1 is 2583, and the preset person quantity threshold is 1000. In this case, the live room 1 is the target live room.

In actual application, if popularity click-farming behavior occurs in a live room, a click-farmer usually uses a fixed machine to simulate a client to perform heartbeat reporting. Therefore, reported IP addresses are centralized, and IP addresses collected by the server are also centralized.

Specifically, the terminal IP address is bound to the location information of the user and is not easily changed. Therefore, the location information of the user can be corresponded according to the terminal IP address. Specifically, the step of collecting user distribution information of a target live room includes:

- determining a user set corresponding to the target live room; and
- collecting location information of each user in the user set, to generate the user distribution information, where the location information includes province information and/or city information.

In actual application, when click-farming in the target live room is determined, a set of users who are viewing livestreaming in the target live room needs to be first obtained, that is, it is necessary to first determine which users are viewing livestreaming content of the target live room.

Then, the location information of each user is successively obtained according to heartbeat information reported by each user in the user set, to generate the user distribution information. In actual application, the location information of the user includes the province information and/or the city information of the user. Still further, the city information may include information such as a prefecture-level city, a county-level city, a district, a county, a village and a town, and a street. A specific form of the city information is not limited in this application.

In a specific implementation provided in this application, the province information is used as an example. Province information corresponding to each user in the live room 1 is obtained, for example, there are 68 persons in Guangdong Province, there are 12 persons in Inner Mongolia, and there are 89 persons in Zhejiang.

In another specific implementation provided in this application, the city information is used as an example. City information corresponding to each user in the live room 1 is obtained, for example, there are 110 persons in Nanjing, there are 70 persons in Suzhou, there are 89 persons in Beijing, and there are 99 persons in Shanghai.

In still another specific implementation provided in this application, the province information and the city information are used as an example. Province information+city information that correspond to each user in the live room 1 are obtained, for example, there are 110 persons in Nanjing-Jiangsu, there are 70 persons in Suzhou-Jiangsu, there are 89 persons in Beijing-Beijing, and there are 99 persons in Shanghai-Shanghai.

After the user distribution information is obtained, the user distribution ratio may be determined based on the user distribution information, specifically including:

- determining the user distribution ratio based on the province information and/or the city information of each user.

The location information of the user specifically includes the province information and/or the city information of the user. Therefore, the user distribution ratio is determined based on the province information and/or the city information of each user. The user distribution ratio specifically is a distribution ratio between user quantities of pieces of location information. For example, the location information is the province information+the city information. A user distribution ratio in a live room is "Nanjing-Jiangsu:Suzhou-Jiangsu: Shanghai-Shanghai:Hangzhou-Zhejiang . . . =10:6:11:8 . . . ", and percentages are 26.6%, 18.6%, 24%, 21.7%, and FIG. 2 is a schematic diagram of a user distribution ratio of a live room according to an embodiment of this application. As shown in FIG. 2, for example, the location information of the user is the province information. A user distribution ratio among Shanghai, Sichuan, Liaoning, Tianjin, and . . . is 254:137:95:62 . . . , and percentages are 29.4%, 16.3%, 12.3%, 10.8%, and . . . .

In a specific embodiment provided in this application, the foregoing example is still used. Collected user distribution information of the live room 1 is that there are 150 persons in Beijing-Beijing, there are 89 persons in Hangzhou-Zhejiang, there are 58 persons in Nanchang-Jiangxi, there are 20 persons in Suzhou-Jiangsu, and . . . Corresponding user distribution ratio is "Beijing-Beijing:Hangzhou-Zhejiang: Nanchang-Jiangxi:Suzhou-Jiangsu . . . =15:9:8:2 . . . ".

Step 104: Obtain population density distribution information, and determine a population density distribution ratio based on the population density distribution information.

The population density distribution information specifically refers to a density distribution situation of a national population. Population density distribution of different provinces and cities is different, which is an inevitable attribute of population distribution. Therefore, real-life population density distribution information can be obtained. Specifically, the population density distribution information may be obtained by using public demographic information, or may be obtained in another way. A specific form of how to obtain the population density distribution information is not limited in this application.

In a specific implementation provided in this application, the step of obtaining population density distribution information includes:

- sending a population density distribution information obtaining request to a statistics server; and
- receiving the population density distribution information returned by the statistics server, where the population density distribution information includes the real-life population density distribution information.

The statistics server may be a server of a statistical department. The statistics server opens a query interface to the outside. Through the query interface, the population density distribution information can be obtained.

After the population density distribution information is obtained, the population density distribution ratio may be further determined according to the population density distribution information based on the foregoing manner of determining the user distribution ratio.

In a specific embodiment provided in this application, the foregoing example is still used. A residential distribution situation (namely, population density distribution information) of a resident population in a past year is obtained from the statistical department. A population density distribution ratio is further determined as "Beijing-Beijing:Hangzhou-Zhejiang:Nanchang-Jiangxi:Suzhou-Jiangsu . . . =20:17:12:3 . . . ", and respective percentages are 28.5%, 19.1%, 16.4%, 4.2%, and . . . .

Step 106: Determine, according to the user distribution ratio and the population density distribution ratio, whether click-farming exists in the target live room.

Under a normal condition, if a population density of a province or a city is relatively large, a viewer quantity of the province or the city is also relatively large. Therefore, whether click-farming exists in a live room can be determined according to a user distribution ratio and a population density distribution ratio of the live room.

Specifically, the step of determining, according to the user distribution ratio and the population density distribution ratio, whether click-farming exists in the target live room includes S1062 to S1066.

S1062: Calculate a distribution variation range according to the user distribution ratio and the population density distribution ratio.

The distribution variation range specifically is a variation range of same location information in a user distribution ratio and a population density distribution ratio. Specifically, the step of calculating a distribution variation range according to the user distribution ratio and the population density distribution ratio includes:

- determining a target user distribution ratio from the user distribution ratio;
- determining a target population density distribution ratio from the population density distribution ratio according to the target user distribution ratio; and
- calculating a target distribution variation range according to the target user distribution ratio and the target population density distribution ratio.

In actual application, the user distribution ratio includes distribution ratios of a plurality of pieces of location information. First, a target user distribution ratio is determined from the user distribution ratio. Next, a target population density distribution ratio is determined from the population density distribution ratio according to location information corresponding to the target user distribution ratio. Then, a target distribution variation range is calculated according to the target user distribution ratio and the target population density distribution ratio. For example, it is determined from the user distribution ratio that a target user distribution ratio of Nanjing-Jiangsu is 26.6%. Then, it is determined from the population density distribution ratio that a target population density distribution ratio of Nanjing-Jiangsu is 28.5%. A target distribution variation range is calculated as 7% according to the target user distribution ratio and the target population density distribution ratio. A plurality of target distribution variation ranges are included in the distribution variation range.

S1064: Determine, if the distribution variation range is less than a preset threshold, that click-farming does not exist in the target live room.

In actual application, the distribution variation range within the preset threshold is considered normal. If the distribution variation range exceeds the threshold, it indicates that click-farming occurs. For example, the preset threshold is 20%. If the distribution variation range is less than the preset threshold, it indicates that click-farming does not exist in the live room.

Specifically, if the target distribution variation range is less than the preset threshold, it is determined that click-farming does not exist in the target live room.

In actual application, the distribution variation range includes the plurality of target distribution variation ranges. If the target distribution variation range is less than the preset threshold, it is determined that click-farming does not exist in the target live room.

S1066: Determine, if the distribution variation range is greater than or equal to the preset threshold, that click-farming exists in the target live room.

Corresponding to S1064, if the distribution variation range is greater than or equal to the preset threshold, it is determined that click-farming exists in the target live room.

Specifically, if the target distribution variation range is greater than or equal to the preset threshold, it is determined that click-farming exists in the target live room.

If the target distribution variation range is greater than or equal to the preset threshold, it is determined that click-farming exists in the target live room.

The foregoing solution is an explanation for determining, according to user distribution, whether click-farming exists in the live room. In actual application, the user distribution of the live room does not necessarily conform to a population distribution density. Different livestreaming content of different live rooms also causes different user distribution. Therefore, further, the method further includes:

- obtaining livestreaming content information of the target live room; and
- when it is determined, according to the user distribution ratio and the population density distribution ratio, that click-farming does not exist in the target live room, determining, according to the livestreaming content information and the user distribution ratio, whether click-farming exists in the target live room.

Specifically, in actual application, it is not precise enough to determine, only by using the user distribution ratio and the population density distribution ratio, whether click-farming exists in the live room. To further improve precision of determining whether click-farming exists in the live room, whether click-farming exists in the target live room may be further determined with reference to the livestreaming content information of the target live room. Different livestreaming content of live rooms also causes a large difference in viewer distribution ratios. For example, if a live room is a live room in Cantonese, a proportion of viewers in Guangdong is relatively high in the live room. For another example, if content of a province/city is introduced in a live room, a proportion of viewers in the province or the city is relatively high.

Correspondingly, in a specific implementation provided in this application, the livestreaming content information includes livestreaming language information.

The determining, according to the livestreaming content information and the user distribution ratio, whether click-farming exists in the target live room includes:

- determining target user language information according to the user distribution ratio; and determining, if the target user language information successfully matches the livestreaming language information, that click-farming does not exist in the target live room; or determining, if the target user language information fails to match the livestreaming language information, that click-farming exists in the target live room.

In this implementation, the obtained livestreaming content information is the livestreaming language information. Language information corresponding to location information with a highest user ratio from the user distribution ratio is determined as the target user language information. When the livestreaming language information matches the target user language information, it indicates that click-farming does not exist in the live room.

Figure 3:
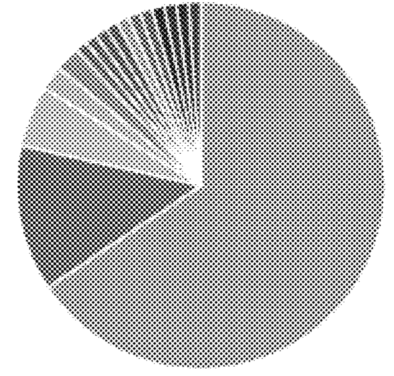
FIG. 3 is a schematic diagram of a user distribution ratio of a live room according to another embodiment of this application.
Figure 3:

Specifically, a comparison table between a province/city and language information may be preconfigured, target location information may be determined according to the user distribution ratio, and then the target user language information may be determined according to the comparison table. For example, refer to FIG. 3. FIG. 3 is a schematic diagram of a user distribution ratio of a live room according to an embodiment of this application. As shown in FIG. 3, Guangdong has a largest viewer quantity in the live room. By using the comparison table between a province/city and language information, it may be determined that target user language information corresponding to Guangdong is Cantonese.

If the livestreaming language information of the live room is also Cantonese, it indicates that the target user language information successfully matches the livestreaming language information, and it is further determined that click-farming does not exist in the target live room.

It is assumed that the livestreaming language information of the live room is Cantonese. However, it is determined, according to live room users, that Liaoning Province has a largest person quantity. Target user language information corresponding to Liaoning Province is a Liaoning dialect. In this case, the target user language information fails to match the livestreaming language information, and it is further determined that click-farming exists in the target live room.

In actual application, a difference in dialects between provinces/cities may be relatively small. For example, for provinces of Heilongjiang, Jilin, and Liaoning, Heilongjiang corresponds to a Heilongjiang dialect, Jilin corresponds to a Jilin dialect, and Liaoning corresponds to the Liaoning dialect. A difference among these three types of dialect information is relatively small. To distinguish language information with a relatively small difference, the target user language information may be further converted into a target user language information vector, and the livestreaming language information is converted into a livestreaming language information vector. Then, a vector similarity between the target user language information vector and the livestreaming language information vector is calculated. If the vector similarity is less than a preset threshold, it indicates that the target user language information successfully matches the livestreaming language information. If the vector similarity is greater than or equal to the preset threshold, it indicates that the target user language information fails to match the livestreaming language information.

In another specific implementation provided in this application, the livestreaming content information includes livestreaming introduction information and/or livestreaming bullet-screen comment information; and the determining, according to the livestreaming content information and the user distribution ratio, whether click-farming exists in the target live room includes:

determining a target keyword according to the livestreaming introduction information and/or the livestreaming bullet-screen comment information;

determining target user region information according to the user distribution ratio;

calculating a degree of association between the target keyword and the target user region information; and determining, if the degree of association is greater than a preset degree of association threshold, that click-farming does not exist in the target live room; or determining, if the degree of association is less than or equal to the preset degree of association threshold, that click-farming exists in the target live room.

In actual application, the livestreaming content information may further include the livestreaming introduction information and/or the livestreaming bullet-screen comment information. The livestreaming introduction information specifically refers to introduction text of the livestreaming content of the live room, and the like. The livestreaming bullet-screen comment information specifically refers to bullet-screen comment information and the like published by a viewer during livestreaming.

The target keyword is entity information in the livestreaming introduction information and/or the livestreaming bullet-screen comment information, and may be a place name, language information, and the like.

The target keyword may be independent of the region information. For example, the livestreaming introduction information includes "Sun Yat-sen Mausoleum introduced in this livestreaming . . . ", and in this case, the target keyword may be determined as "Sun Yat-sen Mausoleum". A bullet-screen comment includes "Roujiamo smells so good", and in this case, the target keyword may be determined as "Roujiamo".

The target keyword may alternatively be related to the region information. For example, during livestreaming, a user always publishes bullet-screen comments such as "Leshan Giant Buddha is so spectacular", and in this case, the target keyword may be obtained through splitting as "Leshan Giant Buddha".

It should be noted that, push stream information of a livestreaming stream may be further obtained from the livestreaming introduction information. For example, it is determined, from livestreaming introduction information of specific livestreaming, that a push stream area of the livestreaming is B City, A Province. Specific content of the livestreaming is an opening ceremony of a specific school, and in this case, a target key "B City, A Province" may be further determined according to the push stream area of the livestreaming stream.

In addition, the target user region information may be further determined according to the user distribution ratio. Specifically, region information with a highest proportion is determined according to the user distribution ratio. Location information with a highest person quantity is determined as the target user region information according to the user distribution ratio. For example, if location information with a highest ratio in the user distribution ratio is "M city", the target user region information is determined as "M city". If the location information with the highest ratio is "N Province", the target user region information is determined as "N Province".

After the target keyword and the target user region information are obtained, the degree of association between the target keyword and the target user region information needs to be further calculated. For example, if a target keyword is “Sun Yat-sen Mausoleum”, and target user region information is “Nanjing, Jiangsu”, a degree of association between “Sun Yat-sen Mausoleum” and “Nanjing, Jiangsu” needs to be further calculated. If a target keyword is “Leshan Giant Buddha” and target user region information is “Leshan, Sichuan”, a degree of association between “Leshan Giant Buddha” and “Leshan, Sichuan” needs to be further calculated. If a target keyword is “B City, A Province” and target user region information is also “B City, A Province”, a degree of association between “B City, A Province” and “B City, A Province” needs to be further calculated.

In a specific calculation mode, the two may be separately converted into vectors, and then a similarity between the two vectors may be calculated. Alternatively, the target keyword and the target user region information may be input into a pre-trained artificial intelligence model, to obtain the degree of association between the target keyword and the target user region information. A specific method for calculating the degree of association between the target keyword and the target user region information is not limited in this application.

If the degree of association is greater than the preset degree of association threshold, it indicates that the livestreaming content of the live room has a local characteristic and regionality, and a viewer of the live room is positively correlated with the local characteristic and the regionality, so that it is determined that click-farming does not exist in the live room.

If the degree of association is less than or equal to the preset degree of association threshold, for example, the live room introduces related content of Sichuan, and user region information of viewers is Hainan, it indicates that click-farming exists in the live room.

Figure 4:
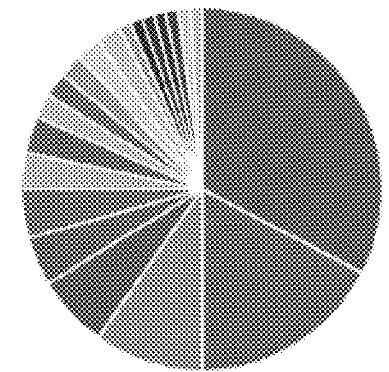
FIG. 4 is a schematic diagram of a user distribution ratio of a live room according to still another embodiment of this application.
Figure 4:

FIG. 4 is a schematic diagram of a user distribution ratio of a live room according to an embodiment of this application. The live room is livestreaming of an activity of a middle school in Hebei Province, and a quantity of viewers in Hebei Province takes up a highest proportion in the live room. By extracting from livestreaming information of the live room, a push stream area of a livestreaming stream of the room is B City, Hebei. Specific livestreaming content is an opening ceremony of a specific middle school in B City, and the livestreaming content belongs to a special local activity. In this case, a proportion of viewers in Hebei Province is relatively high in the live room, so that it can be further determined that the live room does not belong to a click-farmer room.

In actual application, a playing address needs to be requested from a scheduling system each time a live room is entered. Theoretically, distribution of an area sending a request to the scheduling system should also conform to the population density distribution. When a normal client enters the live room, a playing address request is sent to the scheduling system, and a quantity of times of using a same playing address request is limited. Based on this, the method further includes:

- obtaining a scheduling request information set of the target live room;
- querying a quantity of reuse times corresponding to each piece of scheduling request information in the scheduling request information set; and
- determining, if scheduling request information whose quantity of reuse times is greater than a preset times threshold exists in the scheduling request information set, that click-farming exists in the target live room; or
- determining, if the scheduling request information whose quantity of reuse times is greater than the preset times threshold does not exist in the scheduling request information set, that click-farming does not exist in the target live room.

The scheduling request information set of the target live room is obtained, and the scheduling request information set includes a scheduling request indirectly received by the target live room. Then, the quantity of reuse times of each piece of scheduling request information is queried. Specifically, the quantity of reuse times is a quantity of persons who enter the target live room by using the scheduling request information. For example, there are three persons who enter the target live room by using the scheduling request information, and in this case, the quantity of reuse times of the scheduling request information is 3. A purpose of obtaining the playback address by the click-farmer is to simulate a heartbeat. Therefore, scheduling request information is sent only once, and the scheduling request information is subsequently reused to simulate the heartbeat.

Correspondingly, if the scheduling request information whose quantity of reuse times is greater than the preset times threshold exists in the scheduling request information set, it can be determined that click-farming exists in the target live room. If the scheduling request information whose quantity of reuse times is greater than the preset times threshold does not exist in the scheduling request information set, it is determined that click-farming does not exist in the target live room.

The methods for determining click-farming in a live room mentioned in the foregoing embodiments may be used together, for example, a combination of the quantity of reuse times in the scheduling request information set and the user distribution; a combination of the quantity of reuse times in the scheduling request information set, the user distribution, and the user language information; a combination of the quantity of reuse times in the scheduling request information set, the user distribution, and the livestreaming introduction information and/or the livestreaming bullet-screen comment information; a combination of the user distribution, the user language information, and the livestreaming introduction information and/or the livestreaming bullet-screen comment information; or a combination of the quantity of reuse times in the scheduling request information set, the user distribution, the user language information, and the livestreaming introduction information and/or the livestreaming bullet-screen comment information. A combination form of the methods for determining click-farming in a live room is not limited in this application, and is subject to actual application.

The method for determining click-farming in a live room provided in this embodiment of this application includes: determining a target live room; collecting user distribution information of the target live room, and determining a user distribution ratio based on the user distribution information; obtaining population density distribution information, and determining a population density distribution ratio based on the population density distribution information; and determining, according to the user distribution ratio and the population density distribution ratio, whether click-farming exists in the target live room. According to the method for determining click-farming in a live room provided in this application, the user distribution density of the live room is monitored, and whether click-farming exists in the live room is determined with reference to actual population density.

This enriches means for determining click-farming in the live room, and effectively improves accuracy of determining click-farming.

In addition, click-farming in the room may be determined with reference to playback content of the live room, for example, livestreaming voice information, livestreaming region information, and livestreaming push stream information, and combined with the user distribution ratio in the live room, further enriching means for determining click-farming in the live room.

In addition, whether click-farming exists in the live room may be comprehensively determined with reference to a quantity of reuse times of a scheduling request in the live room, enriching means for determining whether click-farming exists in the live room.

Figure 5:
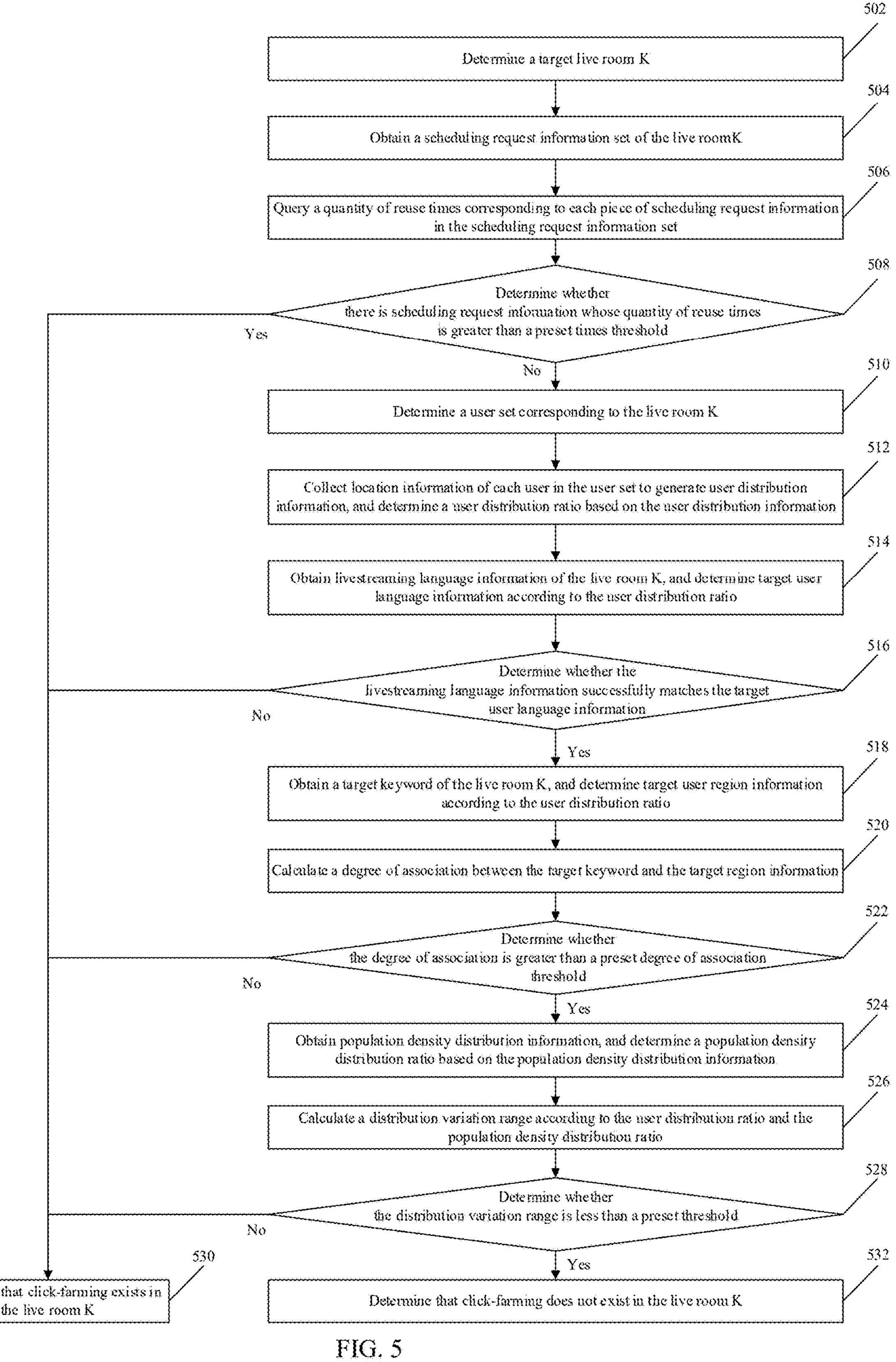
FIG. 5 is a processing flowchart of a method for determining click-farming in a live room applied to determining whether click-farming exists in a live room K according to an embodiment of this application.

With reference to FIG. 5, the following further describes the method for determining click-farming in a live room by using an example in which the method for determining click-farming in a live room provided in this application is applied to determine whether click-farming exists in a live room K. FIG. 5 is a processing flowchart of a method for determining click-farming in a live room applied to determining whether click-farming exists in a live room K according to an embodiment of this application. The method specifically includes the following steps:

Step 502: Determine a target live room K.

Step 504: Obtain a scheduling request information set of the live room K.

Step 506: Query a quantity of reuse times corresponding to each piece of scheduling request information in the scheduling request information set.

Step 508: Determine whether there is scheduling request information whose quantity of reuse times is greater than a preset times threshold; and if yes, perform step 530, or if no, perform step 510.

Step 510: Determine a user set corresponding to the live room K.

Step 512: Collect location information of each user in the user set to generate user distribution information, and determine a user distribution ratio based on the user distribution information.

Step 514: Obtain livestreaming language information of the live room K, and determine target user language information according to the user distribution ratio.

Step 516: Determine whether the livestreaming language information successfully matches the target user language information; and if yes, perform step 518, or if no, perform step 530.

Step 518: Obtain a target keyword of the live room K, and determine target user region information according to the user distribution ratio.

Step 520: Calculate a degree of association between the target keyword and the target region information.

Step 522: Determine whether the degree of association is greater than a preset degree of association threshold; and if yes, perform step 524, or if no, perform step 530.

Step 524: Obtain population density distribution information, and determine a population density distribution ratio based on the population density distribution information.

Step 526: Calculate a distribution variation range according to the user distribution ratio and the population density distribution ratio.

Step 528: Determine whether the distribution variation range is less than a preset threshold; and if yes, perform step 532, or if no, perform step 530.

Step 530: Determine that click-farming exists in the live room K.

Step 532: Determine that click-farming does not exist in the live room K.

According to the method for determining click-farming in a live room provided in this application, user distribution density of the live room is monitored, and whether click-farming exists in the live room is determined with reference to actual population density. This enriches means for determining click-farming in the live room, and effectively improves accuracy of determining click-farming.

In addition, click-farming in the room may be determined with reference to playback content of the live room, for example, livestreaming voice information, livestreaming region information, and livestreaming push stream information, and combined with the user distribution ratio in the live room, further enriching means for determining click-farming in the live room.

In addition, whether click-farming exists in the live room may be comprehensively determined with reference to a quantity of reuse times of a scheduling request in the live room, enriching means for determining whether click-farming exists in the live room.

Figure 6:
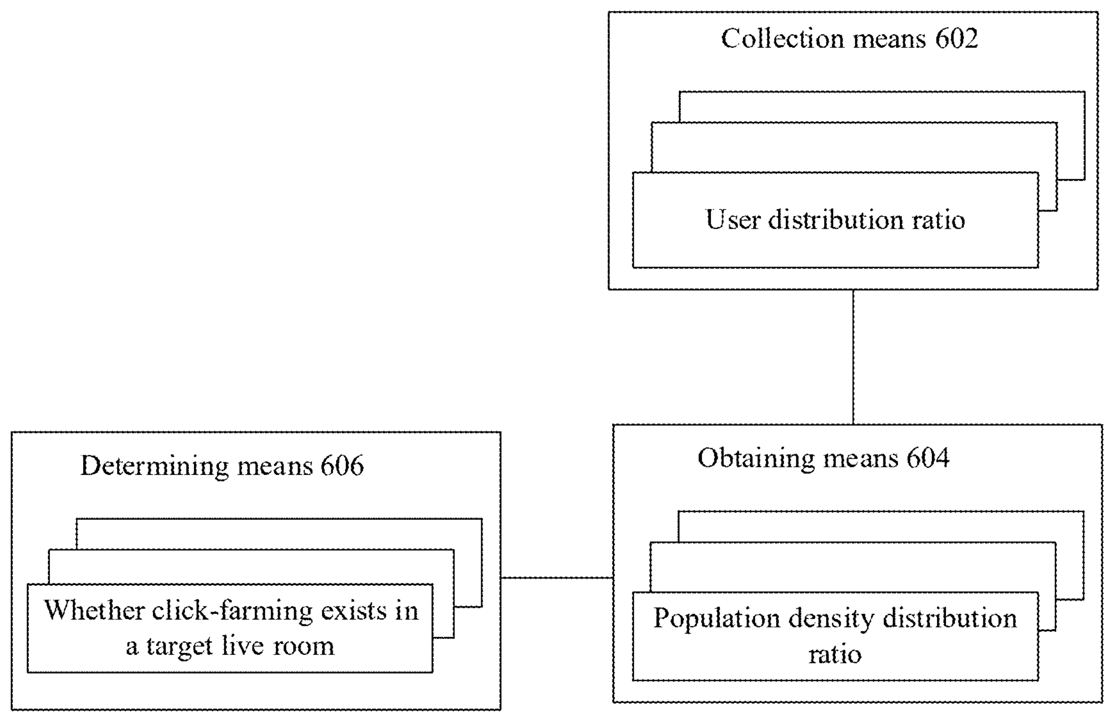
FIG. 6 is a schematic diagram of a structure of an apparatus for determining click-farming in a live room according to an embodiment of this application.

Corresponding to the foregoing embodiments of the method for determining click-farming in a live room, this application further provides an embodiment of an apparatus for determining click-farming in a live room. FIG. 6 is a schematic diagram of a structure of an apparatus for determining click-farming in a live room according to an embodiment of this application. As shown in FIG. 6, the apparatus includes:

- a collection means 602, configured to collect user distribution information of a target live room, and determine a user distribution ratio based on the user distribution information;
- an obtaining means 604, configured to obtain population density distribution information, and determine a population density distribution ratio based on the population density distribution information; and
- a determining means 606, configured to determine, according to the user distribution ratio and the population density distribution ratio, whether click-farming exists in the target live room.

Optionally, the collection means 602 is further configured to:

- determine a user set corresponding to the target live room; and
- collect location information of each user in the user set, to generate the user distribution information, where the location information includes province information and/or city information.

Optionally, the collection means 602 is further configured to:

- determine the user distribution ratio based on the province information and/or the city information of each user.

Optionally, the obtaining means 604 is further configured to:

- send a population density distribution information obtaining request to a statistics server; and
- receive the population density distribution information returned by the statistics server, where the population density distribution information includes real-life population density distribution information.

Optionally, the determining means 606 is further configured to:

- calculate a distribution variation range according to the user distribution ratio and the population density distribution ratio; and determine, if the distribution variation range is less than a preset threshold, that click-farming does not exist in the target live room; or determine, if the distribution variation range is greater than or equal to the preset threshold, that click-farming exists in the target live room.

Optionally, the determining means 606 is further configured to:

determine a target user distribution ratio from the user distribution ratio;

determine a target population density distribution ratio from the population density distribution ratio according to the target user distribution ratio; and calculate a target distribution variation range according to the target user distribution ratio and the target population density distribution ratio.

Optionally, the determining means 606 is further configured to:

determine, if the target distribution variation range is less than the preset threshold, that click-farming does not exist in the target live room; and correspondingly, the determining, if the distribution variation range is greater than or equal to the preset threshold, that click-farming exists in the target live room includes:

determining, if the target distribution variation range is greater than or equal to the preset threshold, that click-farming exists in the target live room.

Optionally, the apparatus further includes:

an information obtaining means, configured to obtain livestreaming content information of the target live room.

Correspondingly, the determining means 606 is further configured to:

determine, according to the livestreaming content information and the user distribution ratio, whether click-farming exists in the target live room.

Optionally, the livestreaming content information includes livestreaming language information.

The determining means 606 is further configured to:

determine target user language information according to the user distribution ratio; and determine, if the target user language information successfully matches the livestreaming language information, that click-farming does not exist in the target live room; or determine, if the target user language information fails to match the livestreaming language information, that click-farming exists in the target live room.

Optionally, the livestreaming content information includes livestreaming introduction information and/or livestreaming bullet-screen comment information.

The determining means 606 is further configured to:

determine a target keyword according to the livestreaming introduction information and/or the livestreaming bullet-screen comment information;

determine target user region information according to the user distribution ratio;

calculate a degree of association between the target keyword and the target user region information; and determine, if the degree of association is greater than a preset degree of association threshold, that click-farming does not exist in the target live room; or determine, if the degree of association is less than or equal to the preset degree of association threshold, that click-farming exists in the target live room.

Optionally, the apparatus further includes:

a request obtaining means, configured to obtain a scheduling request information set of the target live room; and a query means, configured to query a quantity of reuse times corresponding to each piece of scheduling request information in the scheduling request information set.

Correspondingly, the determining means 606 is further configured to:

determine, if scheduling request information whose quantity of reuse times is greater than a preset times threshold exists in the scheduling request information set, that click-farming exists in the target live room; or determine, if the scheduling request information whose quantity of reuse times is greater than the preset times threshold does not exist in the scheduling request information set, that click-farming does not exist in the target live room.

Optionally, the apparatus further includes a room determining means, and the room determining means is configured to:

determine an initial live room on a livestreaming platform, and obtain a live room person quantity of the initial live room; and when the live room person quantity exceeds a preset person quantity threshold, determine the initial live room as a target live room.

The apparatus for determining click-farming in a live room provided in this embodiment of this application is configured to: determine a target live room; collect user distribution information of the target live room, and determine a user distribution ratio based on the user distribution information; obtain population density distribution information, and determine a population density distribution ratio based on the population density distribution information; and determine, according to the user distribution ratio and the population density distribution ratio, whether click-farming exists in the target live room. According to the method for determining click-farming in a live room provided in this application, user distribution density of the live room is monitored, and whether click-farming exists in the live room is determined with reference to actual population density. This enriches means for determining click-farming in the live room, and effectively improves accuracy of determining click-farming.

In addition, click-farming in the room may be determined with reference to playback content of the live room, for example, livestreaming voice information, livestreaming region information, and livestreaming push stream information, and combined with the user distribution ratio in the live room, further enriching means for determining click-farming in the live room.

In addition, whether click-farming exists in the live room may be comprehensively determined with reference to a quantity of reuse times of a scheduling request in the live room, enriching means for determining whether click-farming exists in the live room.

The foregoing describes a schematic solution of the apparatus for determining click-farming in a live room in this embodiment. It should be noted that the technical solution of the apparatus for determining click-farming in a live room and the technical solution of the method for determining click-farming in a live room belong to a same concept. For details not described in detail in the technical solution of the apparatus for determining click-farming in a live room, refer to the descriptions of the technical solution of the method for determining click-farming in a live room.

Figure 7:
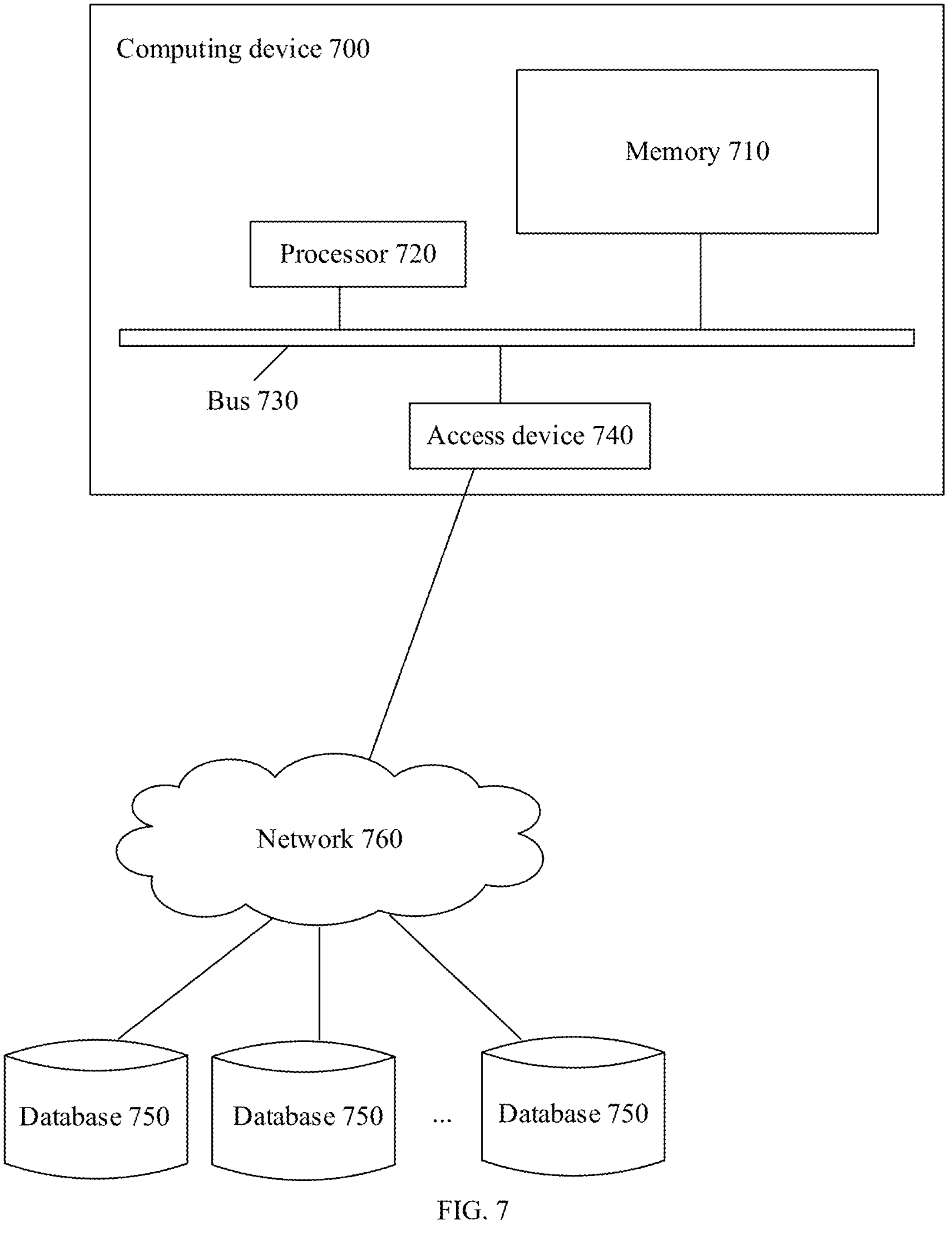
FIG. 7 is a block diagram of a structure of a computing device according to an embodiment of this application.

FIG. 7 is a block diagram of a structure of a computing device 700 according to an embodiment of this application. Components of the computing device 700 include but are not limited to a memory 710 and a processor 720. The processor 720 is connected to the memory 710 by using a bus 730. A database 750 is configured to store data.

The computing device 700 further includes an access device 740. The access device 740 enables the computing device 700 to perform communication by using one or more networks 760. Examples of these networks include a public switched telephone network (PSTN), a local area network (LAN), a wide area network (WAN), a private area network (PAN), or a combination of communication networks such as the Internet. The access device 740 may include one or more of any type of wired or wireless network interface (for example, a network interface card (NIC)), such as an IEEE802.11 wireless local area network (WLAN) wireless interface, a worldwide interoperability for microwave access (Wi-MAX) interface, an Ethernet interface, a universal serial bus (USB) interface, a cellular network interface, a Bluetooth interface, and a near field communication (NFC) interface.

In an embodiment of this application, the foregoing components of the computing device 700 and other components not shown in FIG. 7 may be connected to each other, for example, by using a bus. It should be understood that the block diagram of the structure of the computing device shown in FIG. 7 is merely used as an example instead of a limitation on the scope of this application. A person skilled in the art can add or replace other components as required.

The computing device 700 may be any type of stationary or mobile computing device, including a mobile computer or a mobile computing device (for example, a tablet computer, a personal digital assistant, a laptop computer, a notebook computer, or a netbook), a mobile phone (for example, a smartphone), a wearable computing device (for example, a smartwatch or smart glasses), or another type of mobile device, or a stationary computing device such as a desktop computer or a PC. The computing device 700 may alternatively be a mobile or stationary server.

The processor 720 implements the steps of the method for determining click-farming in a live room when executing computer instructions.

The foregoing describes a schematic solution of the computing device in this embodiment. It should be noted that the technical solution of the computing device and the technical solution of the method for determining click-farming in a live room belong to a same concept. For details not described in detail in the technical solution of the computing device, refer to the descriptions of the technical solution of the method for determining click-farming in a live room.

An embodiment of this application further provides a computer-readable storage medium, storing computer instructions, and the computer instructions are executed by a processor to implement the steps of the method for determining click-farming in a live room.

The foregoing describes a schematic solution of the computer-readable storage medium in this embodiment. It should be noted that the technical solution of the storage medium and the technical solution of the method for determining click-farming in a live room belong to a same concept. For details not described in detail in the technical solution of the storage medium, refer to the descriptions of the technical solution of the method for determining click-farming in a live room.

An embodiment of this application further provides a computer program, and when the computer program is executed in a computer, the computer is enabled to perform the steps of the method for determining click-farming in a live room.

The foregoing describes a schematic solution of the computer program in this embodiment. It should be noted that the technical solution of the computer program and the technical solution of the method for determining click-farming in a live room belong to a same concept. For details not described in detail in the technical solution of the computer program, refer to the descriptions of the technical solution of the method for determining click-farming in a live room.

Specific embodiments of this application are described above. Other embodiments fall within the scope of the appended claims. In some cases, actions or steps described in the claims may be performed in an order different from that in the embodiments and desired results may still be achieved. In addition, processes described in the accompanying drawings do not necessarily require shown specific orders or sequences to achieve the desired results. In some implementations, multitasking and parallel processing are also possible or may be advantageous.

The computer instructions include computer program code, and the computer program code may be in a source code form, an object code form, an executable file form, some intermediate forms, or the like. The computer-readable medium may include: any entity or apparatus, a recording medium, a USB flash drive, a removable hard disk, a magnetic disk, a compact disc, a computer memory, a read-only memory (ROM), a random access memory (RAM), an electrical carrier signal, a telecommunication signal, a software distribution medium, and the like that are capable of carrying the computer program code. It should be noted that the content included in the computer-readable medium can be appropriately added or deleted depending on requirements of the legislation and patent practice in a jurisdiction. For example, in some jurisdictions, according to the legislation and patent practice, the computer-readable medium does not include an electrical carrier signal or a telecommunication signal.

It should be noted that, for brief description, the foregoing method embodiments are represented as a combination of a series of actions. However, a person skilled in the art should be aware that this application is not limited to the described order of the actions, because some steps may be performed in other orders or simultaneously according to this application. In addition, a person skilled in the art should also be aware that the embodiments described in this specification are all example embodiments, and used actions and means are not necessarily mandatory to this application.

In the foregoing embodiments, the descriptions of the embodiments have respective focuses. For a part that is not described in detail in a specific embodiment, refer to related descriptions in other embodiments.

The example embodiments of this application disclosed above are merely intended to help describe this application. In the optional embodiments, not all details are described in detail, and the present invention is not limited to only the specific implementations. Clearly, many modifications and variations may be made based on the content of this application. In this application, these embodiments are selected and specifically described to better explain the principle and actual application of this application, so that a person skilled in the art can well understand and use this application. This application is only subject to the claims and a full scope and equivalents thereof.

What is claimed is:

1. A method for determining click-farming in a live room, comprising:

receiving, at a server of a livestreaming platform, periodic heartbeat signals reported by client computing devices associated with users currently viewing a target live room, wherein the heartbeat signals reported by the client computing devices comprise IP addresses of the client computing devices;

determining user distribution information associated with a target live room of the livestreaming platform by determining location information of the users based on the IP addresses of the client computing devices associated with the users, and determining a user distribution ratio based on the user distribution information;

obtaining population density distribution information, and determining a population density distribution ratio based on the population density distribution information;

determining whether click-farming exists in the target live room based on the user distribution ratio and the population density distribution ratio by determining, for each region, a distribution variation and determining that click-farming exists when at least one distribution variation for a region is greater than or equal to a preset threshold; and automatically initiating a punishment action with respect to the target live room in which click-farming exists.

2. The method according to claim 1, wherein the determining user distribution information associated with a target live room comprises:

determining a set of users corresponding to the target live room; and generating the user distribution information based on the location information of each user, wherein the location information comprises at least one of province information or city information of each user.

3. The method according to claim 2, wherein the determining a user distribution ratio based on the user distribution information comprises:

determining a quantity of users from the set of users associated with a same piece of location information; and determining the user distribution ratio based on quantities of users associated with different pieces of location information.

4. The method according to claim 1, wherein the obtaining population density distribution information comprises:

sending a request for obtaining the population density distribution information to a statistics server; and receiving the population density distribution information returned by the statistics server, wherein the population density distribution information comprises real-life population density distribution information.

5. The method according to claim 1, wherein the determining whether click-farming exists in the target live room based on the user distribution ratio and the population density distribution ratio comprises:

computing a distribution variation associated with each piece of location information based on the user distribution ratio and the population density distribution ratio; and determining that click-farming does not exist in the target live room in response to determining that the distribution variation is less than the preset threshold; and determining that click-farming exists in the target live room in response to determining that the distribution variation is greater than or equal to the preset threshold.

6. The method according to claim 5, wherein the computing a distribution variation associated with each piece of location information based on the user distribution ratio and the population density distribution ratio comprises:

determining a target user distribution ratio associated with a particular piece of location information based on the user distribution ratio;

determining a target population density distribution ratio based on the population density distribution ratio and the particular piece of location information; and computing a target distribution variation based on a difference of the target user distribution ratio relative to the target population density distribution ratio.

7. The method according to claim 6, wherein the determining that click-farming does not exist in the target live room in response to determining that the distribution variation is less than a preset threshold comprises determining that click-farming does not exist in the target live room in response to determining that the target distribution variation is less than the preset threshold; and wherein the determining that click-farming exists in the target live room in response to determining that the distribution variation is greater than or equal to the preset threshold comprises determining that click-farming exists in the target live room in response to determining that the target distribution variation is greater than or equal to the preset threshold.

8. The method according to claim 1, further comprising:

obtaining information associated with livestreaming content of the target live room; and determining whether click-farming exists in the target live room based on the information associated with the livestreaming content and the user distribution ratio in response to determining that click-farming does not exist in the target live room based on the user distribution ratio and the population density distribution ratio.

9. The method according to claim 8, wherein the information associated with the livestreaming content comprises a livestreaming language of a livestream in the target live room; and wherein the determining whether click-farming exists in the target live room based on the information associated with the livestreaming content and the user distribution ratio comprises:

determining a target user language based on the user distribution ratio;

determining that click-farming does not exist in the target live room in response to determining that the target user language matches the livestreaming language; and determining that click-farming exists in the target live room in response to determining that the target user language fails to match the livestreaming language.

10. The method according to claim 8, wherein the information associated with the livestreaming content comprises at least one of an introduction of a livestream in the target live room or bullet-screen comments on the livestream; and wherein the determining whether click-farming exists in the target live room based on the livestreaming content and the user distribution ratio comprises:

determining a target keyword based on the at least one of the introduction of the livestream or the bullet-screen comments on the livestream;

determining a target region based on the user distribution ratio, wherein the target region corresponds to a piece of location information with a highest value in the user distribution ratio;

calculating a degree of association between the target keyword and the target region;

determining that click-farming does not exist in the target live room in response to determining that the degree of association is greater than a preset association threshold; and determining that click-farming exists in the target live room in response to determining that the degree of association is less than or equal to the preset association threshold.

11. The method according to claim 1, further comprising:

obtaining a set of scheduling information associated with the target live room;

querying a quantity of reuse times for entering the target live room by reusing each piece of scheduling information in the set of the scheduling request information, wherein each piece of scheduling information comprises a playing address associated with the target live room;

determining that click-farming exists in the target live room in response to determining that a piece of scheduling information with reuse times being greater than a preset threshold exists in the set of the scheduling information; and determining that click-farming does not exist in the target live room in response to determining that no piece of scheduling information with reuse times being greater than the preset threshold exists in the set of the scheduling information.

12. The method according to claim 1, further comprising:

determining an initial live room on the livestreaming platform, and obtaining a quantity of users in the initial live room; and determining the initial live room as the target live room in response to determining that the quantity of users exceeds a preset user quantity threshold.

13. A computing device, comprising a memory, a processor, and computer instructions stored in the memory and executable by the processor, wherein the computer instructions upon execution by the processor cause the processor to implement operations comprising:

receiving, at a server of a livestreaming platform, periodic heartbeat signals reported by client computing devices associated with users currently viewing a target live room, wherein the heartbeat signals reported by the client computing devices comprise IP addresses of the client computing devices;

determining user distribution information associated with a target live room of the livestreaming platform by determining location information of the users based on the IP addresses of the client computing devices associated with the users, and determining a user distribution ratio based on the user distribution information;

obtaining population density distribution information, and determining a population density distribution ratio based on the population density distribution information;

determining whether click-farming exists in the target live room based on the user distribution ratio and the population density distribution ratio by determining, for each region, a distribution variation and determining that click-farming exists when at least one distribution variation for a region is greater than or equal to a preset threshold; and automatically initiating a punishment action with respect to the target live room in which click-farming exists.

14. The computing device according to claim 13, wherein the determining user distribution information associated with a target live room comprises:

determining a set of users corresponding to the target live room; and generating the user distribution information based on the location information of each user, wherein the location information comprises at least one of province information or city information of each user.

15. The computing device according to claim 14, wherein the determining a user distribution ratio based on the user distribution information comprises:

determining a quantity of users from the set of users associated with a same piece of location information; and determining the user distribution ratio based on quantities of users associated with different pieces of location information.

16. The computing device according to claim 13, wherein the determining whether click-farming exists in the target live room based on the user distribution ratio and the population density distribution ratio comprises:

computing a distribution variation associated with each piece of location information based on the user distribution ratio and the population density distribution ratio, wherein the computing a distribution variation associated with each piece of location information based on the user distribution ratio and the population density distribution ratio comprises:

determining a target user distribution ratio associated with a particular piece of location information based on the user distribution ratio, determining a target population density distribution ratio based on the population density distribution ratio and the particular piece of location information, and computing a target distribution variation based on a difference of the target user distribution ratio relative to the target population density distribution ratio;

determining that click-farming does not exist in the target live room in response to determining that the target distribution variation is less than a preset threshold; and determining that click-farming exists in the target live room in response to determining that the target distribution variation is greater than or equal to the preset threshold.

17. The computing device according to claim 13, the operations further comprising:

obtaining information associated with livestreaming content of the target live room; and determining whether click-farming exists in the target live room based on the information associated with the livestreaming content and the user distribution ratio.

18. The computing device according to claim 17, wherein the information associated with the livestreaming content comprises a livestreaming language of a livestream in the target live room, and wherein the determining whether click-farming exists in the target live room based on the information associated with the livestreaming content and the user distribution ratio comprises:

determining a target user language based on the user distribution ratio;

determining that click-farming does not exist in the target live room in response to determining that the target user language matches the livestreaming language; and determining that click-farming exists in the target live room in response to determining that the target user language fails to match the livestreaming language.

19. A non-transitory computer-readable storage medium, storing computer instructions, wherein the computer instructions upon execution by a processor cause the processor to implement operations comprising:

receiving, at a server of a livestreaming platform, periodic heartbeat signals reported by client computing devices associated with users currently viewing a target live room, wherein the heartbeat signals reported by the client computing devices comprise IP addresses of the client computing devices;

determining user distribution information associated with a target live room of the livestreaming platform by determining location information of the users based on the IP addresses of the client computing devices associated with the users, and determining a user distribution ratio based on the user distribution information;

obtaining population density distribution information, and determining a population density distribution ratio based on the population density distribution information;

determining whether click-farming exists in the target live room based on the user distribution ratio and the population density distribution ratio by determining, for each region, a distribution variation and determining that click-farming exists when at least one distribution variation for a region is greater than or equal to a preset threshold; and automatically initiating a punishment action with respect to the target live room in which click-farming exists.

* * * * *